United States Patent [19]

Bortinger

[11] Patent Number: 5,280,003
[45] Date of Patent: Jan. 18, 1994

[54] STATIC CONDITION PROCESS FOR THE PREPARATION OF PHOSPHOROUS/VANADIUM OXIDATION CATALYST

[75] Inventor: Arie Bortinger, Ridgewood, N.J.

[73] Assignee: Scientific Design Company, Inc., Little Ferry, N.J.

[21] Appl. No.: 933,696

[22] Filed: Aug. 24, 1992

[51] Int. Cl.$^5$ .................. B01J 37/16; B01J 37/03; B01J 27/18; B01J 27/19
[52] U.S. Cl. ........................................... 502/209
[58] Field of Search ................................ 502/209

[56] References Cited

U.S. PATENT DOCUMENTS

| | | | |
|---|---|---|---|
| 3,255,211 | 6/1966 | Kerr | 502/209 X |
| 4,017,521 | 4/1977 | Schneider | 549/259 |
| 4,043,943 | 8/1977 | Schneider | 502/209 |
| 4,056,487 | 11/1977 | Kerr | 502/209 |
| 4,105,586 | 8/1978 | Kerr | 502/209 |
| 4,147,661 | 4/1979 | Higgins et al. | 502/209 |
| 4,418,003 | 11/1983 | Udovich et al. | 502/209 |
| 4,515,899 | 5/1985 | Click et al. | 502/209 X |
| 4,632,915 | 12/1986 | Keppel et al. | 502/209 |
| 4,668,652 | 5/1987 | Fumagalli et al. | 502/209 |
| 4,670,415 | 6/1987 | Keppel et al. | 502/209 |
| 5,070,060 | 12/1991 | Barone | 502/209 |

FOREIGN PATENT DOCUMENTS 0466480  1/1992  European Pat. Off. ............ 502/209

*Primary Examiner*—W. J. Shine
*Assistant Examiner*—Douglas J. McGinty
*Attorney, Agent, or Firm*—Kenneth H. Johnson

[57] ABSTRACT

An improvement in the oxidation catalyst used for the partial oxidation of n-butane and containing vanadium and phosphorus, zinc, lithium and molybdenum mixed oxides which comprises carrying out the crystallization step under static conditions which allows for more uniform conditions for crystal growth. The static conditions are maintained by refluxing the solvent during the period of crystallization.

14 Claims, No Drawings

STATIC CONDITION PROCESS FOR THE PREPARATION OF PHOSPHOROUS/VANADIUM OXIDATION CATALYST

BACKGROUND OF THE INVENTION

The present invention relates to a method for producing molybdenum containing PVO-zinc activated, lithium modified catalyst for use the in the partial oxidation of hydrocarbons to prepare dicarboxylic acids and anhydrides. More particularly, the invention relates to an anhydrous system for the preparation of phosphorus-vanadium mixed oxide catalyst.

Basically, all of the methods used to prepare oxidation catalysts seek to obtain vanadium in a valence state of less than +5. One method of achieving this is to begin with vanadium in less than the +5 valence state. Another method and that used most widely in the art is to start with vanadium in the +5 state and reduce the valency to less than +5. This invention relates to the latter method. Several variations on this method have been used to obtain these catalyst. In one method $V_2O_5$ is reduced in a solution with HCl to obtain vanadyl chloride. A typical catalyst preparation may involve dissolving the vanadium, phosphorus, and other components in a common solvent. The reduced vanadium with a valence of less than 5 is obtained by initially using a vanadium compound with a valence of plus 5 such as $V_2O_5$ and thereafter reducing to the lower valence with, for example, hydrochloric acid during the catalyst preparation to form the vanadium oxysalt, vanadyl chloride, in situ. The vanadium compound is dissolved in a reducing solvent, such as hydrochloric acid reduces the valence of the vanadium compound to a valence of less than 5 and functions as a solvent for the reaction. Preferably, the vanadium compound is first dissolved in the hydrochloric acid and thereafter the phosphorus and other components, if any, are added. The reaction to form the complex may be accelerated by the application of heat. The complex formed is then, without a precipitation step, deposited as a solution onto a carrier and dried. Generally, the average valence of the vanadium will be between about plus 2.5 and 4.6 at the time of deposition onto the carrier.

In another method the catalyst is prepared by precipitating the metal compounds, either with or without a carrier, from a colloidal dispersion of the ingredients in an inert liquid. In some instances the catalyst may be deposited as molten metal compounds onto a carrier. The catalysts have also been prepared by heating and mixing anhydrous forms of phosphorus acids with vanadium compounds and other components. In any of the methods of preparation, heat may be applied to accelerate the formation of the complex.

A method of obtaining vanadyl chloride was disclosed by Koppel et al, Zeit. Anorg. Chem, 45, p. 346-351, 1905 by the reduction of $V_2O_5$ in alcoholic HCl solution. This method had been recommended for the preparation of the phosphorus-vanadium oxidation catalyst for example, by Kerr in U.S. Pat. No. 3,255,211 where the solvent also serves as the reducing agent. Subsequently, U.S. Pat. Nos. 4,043,943, 4,251,390, 4,283,307; and 4,418,003 for example, employed this method generally referred to as the "anhydrous process" of reducing vanadium to prepare the basic phosphorus-vanadium catalyst. The catalysts produced by this latter method have been found to be generally superior to similar catalyst by the other methods. Specifically what had occurred to this class of oxidation catalysts prior to the return to the anhydrous process had been the addition of a veritable cornucopia of elements to the base vanadium-phosphorus composition, see for example U.S. Pat. No. 4,105,586 where in addition to V, P and O the catalyst must contain nine other elements. The catalyst were satisfactory, but manufacturing was difficult because of the number of components and their varying effects on the catalyst performance.

The anhydrous system went back to the basics with the Schneider procedure in U.S. Pat. No. 4,043,943 with only V, P and O. However, this catalyst required a very specific activation procedure as described, for example in U.S. Pat. No. 4,017,521. Barone (U.S. Pat. No. 4,251,390) showed that the addition of Zn alleviated the need for the specific activation process and produced a catalyst which was more easily activated and which was very stable to heat upset of the reaction system as well as exhibiting equal or superior performance (conversion/selectivity/yield) to the base catalyst. Small amounts of silicon and lithium compounds were also found to enhance the catalytic effects of P/V/Zn catalyst.

U.S. Pat. No. 4,147,661 discloses high surface area PVO mixed oxide catalyst additionally containing W, Sb, Ni and/or Mo at atomic ratios of 0.0025 to 1:1 to vanadium.

A particular problem facing all of the PVO containing catalysts is the loss of phosphorus, a discussion of this problem and various solutions is found in U.S. Pat. No. 4,515,899.

Many references disclosing oxidation catalysts which are suitable for producing maleic anhydride by the partial oxidation of n-butane, which catalysts contain molybdenum as one component of a phosphorus, vanadium mixed oxide catalyst. For example U.S. Pat. No. 3,980,585 discloses a catalyst containing P, V Cu and one of Te, Zr, Ni, Ce, W, Pd, Ag, Mn, Cr, Zn, Mo, Re, Sn, La, Hf Ta, Th, Ca, U or Sn; and U.S. Pat. No. 4,056,487 discloses a PVO catalyst containing Nb, Cu, Mo, Ni, Co and plus one or more of Ce, Nd, Ba, Hf, U, Ru, Re, Li or Mg. U.S. Pat. No. 4,515,904 discloses a procedure for preparing PVO catalysts which may include one metal of Mo, Zn, W, U, Sn, Bi, Ti, Zr, Ni, Cr or Co in atomic ratios of metal: V of 0.001 to 0.2:1.

U.S. Pat. No. 4,418,003 discloses PVO catalysts containing either Zn or Mo which is deactivated by Na or Li and which may also contain Zr, Ni, Ce, Cr, Mn, Ni and Al.

Commonly owned U.S Pat. No. 5,070,060, which discloses PVO mixed oxide Mo containing oxidation catalyst is incorporated herein.

It is a feature of the present invention that the crystallization occurs under static conditions which allow more uniform conditions for crystal growth. It is another feature of the invention that the crystallization step can be followed by following the drop in reaction temperature.

SUMMARY OF THE INVENTION

The present invention lies in an improvement in an anhydrous process for manufacturing a phosphorus/vanadium/zinc/lithium mixed oxide oxidation catalyst containing from 0.005 to 0.025 atoms of molybdenum per atom of vanadium. Most particularly the invention relates to a method of preparing the catalyst wherein the crystallization occurs under static conditions which allows for more uniform conditions for crystal growth. The present catalysts ar produced by the process comprising reducing vanadium in the +5 valence state in a substantially anhydrous organic medium to a valence of less than +5 and digesting said reduced vanadium in concentrated phosphoric acid wherein the improvement comprises (1) refluxing the solvent for a first period, (2) removing a portion of the solvent by distillation to initiate crystallization, (3) refluxing the solvent again for a second period during which the crystallization is substantially completed and (4) removing the remainder of the solvent. The use of a cosolvent system has been found to be beneficial.

PREFERRED EMBODIMENTS

More specifically, the present catalyst is that produced from an alcoholic HCl solution reduction of vanadium pentoxide wherein the organic solvent is a alcohol and the reduction of the vanadium is obtained by contacting it with HCl. This is conveniently carried out by passing gaseous HCl through the alcohol having the vanadium pentoxide suspended therein. The vanadium pentoxide is reduced by the HCl and brought into solution as the vanadyl chloride. The completion of the reduction is the appearance of a dark reddish brown solution. Hydrogen bromide would be about the same as a reducing agent in this system. It is preferred that the reduction temperature should be maintained at no greater than 60° C. and preferably less than 55° C. Optimally active catalyst are the result when the reduction is carried out temperatures in the range of about 35 C to 55° C., preferably 40° C. to 55° C.

Generally in the catalyst preparation from 2500 to 4400 ml of alcohol, preferably 3100 to 4200 ml per pound of $V_2O_5$ and from 1.5 to 3.0 pounds of HCl per pound of $V_2O_5$ are employed.

To obtain the mixed oxides of vanadium and phosphorus, phosphoric acid of approximately 99% $H_3PO_4$ (98 to 101%) is added, for example, prepared from 85 $H_3PO_4$ and $P_2O_5$ or commercial grades of 105 and 115% phosphoric acid diluted with 85% $H_3PO_4$ and the vanadium compound digested which is discerned by a change in the color of the solution to a dark blue green. The digestion of the vanadium compound in the phosphoric acid is conducted at reflux until the color change indicated the completed digestion. Prior to the first reflux a minor portion, 1–5% by volume of the alcohol solvent is distilled out of the reaction solution. The remaining alcohol is stripped off in two stages to obtain the dried catalyst. Each of the two stages comprise refluxing the solvent for about 15 minutes to 10 hours, preferably about an hour followed by stripping of about 20–85 vol % of the solvent after the first stage refluxing step and about 40–85 vol % of the solvent remaining after the second refluxing step. Solvent remaining after the two stripping steps is removed by drying under less rigorous conditions.

The final removal of alcohol is usually carried out in an oven at a temperature in the range of 110° to 170° C. Reduced pressure can also be applied to lower oven temperatures. Generally calcination or roasting of the dried catalyst will be at a temperature in the range of 200° to 400 C. for a sufficient period to improve the catalytic properties of the composition.

The temperatures employed are relatively low hence the term calcination may not be appropriate. In any event, heating the composition under these temperature conditions has been found beneficial. The calcination is preferably carried out to produce materials having a characteristic powder x-ray diffraction ratio.

The organic solvent is preferably a primary or secondary alcohol such as methanol, ethanol, 1-propanol, 2-propanol, butanol, 2-butanol, 2,methyl-1-propanol, 3-methyl-2-butanol, 2,2-dimethyl-1-propanol, 1-hexanol, 4-methyl-1-pentanol, 1-heptanol, 4-methyl-1-hexanol, 4-methyl-1-heptanol, 1,2-ethanediol, glycerol, trimethylopropane, 4-methyl 2-pentanone, diethylene glycol and triethylene glycol or mixtures thereof. The alcohol is also a mild reducing agent for the vanadium +5 compound. A preferred cosolvent system comprises 2-butanol and from 5–50 vol % of the cosolvent, e.g. isobutanol.

Generally the atomic ratio of Zn to vanadium is in the range of 0.001 to 0.15:1, however it has been found that lower ratios of zinc/vanadium produce the most active catalyst and compositions containing Zn/V mole ratio in the range of 0.01 to 0.07 are preferred.

The phosphorus is generally present in these catalyst as well as those of the prior art in the mole ration of P/V 0.09–1.3/1. Optimum ratios P/V are found to be below 1.22/1 and above 1.0/1. The stabilizing effect of Mo allows the use of less phosphorus than otherwise comparable prior art catalyst and the concomitant benefit that phosphorus loss and the resulting deactivation of the catalyst in reactor operation is reduced, i.e., longer time trend (reactivity vs hours on stream).

The lithium component is present at an atomic ratio of 0.001 to 0.15:1, Li:V.

The point at which the zinc component, lithium component and molybdenum component is added is not critical so long it is present prior to formation of the solid catalyst precipitate. This is conveniently done along with the phosphoric acid addition, thereby assuring the intimate mixing of the catalyst components.

The modifier components are added as the compounds thereof such as acetates, carbonates, chlorides, bromides, oxides, hydroxides, phosphates and the like e.g., zinc chloride, zinc oxide, zinc oxalate, lithium acetate, lithium chloride, lithium bromide, lithium carbonate, lithium oxide, lithium orthophosphate, molybdenum oxide, molybdenum dioxydichloride, molybdenum dioxydibromide and the like.

The resultant catalyst complex is characterized as a mixed oxide, however, the structure of the complex has not been determined but may be conveniently represented by a formula such as:

$$V\ P_a\ Zn_b\ Mo_c\ Li_d\ O_x$$

a is 0.90 to 1.3, b is 0.001 to 0.15, c is 0.005 to 0.025 and d is 0.001 to 0.15. This representation is not an empirical formula and has no significance other than representing the atom ratio of the components of the catalyst. The x in fact, has no determinate value and can vary widely depending on the combinations within the complex. That there is oxygen present is known, and the $O_x$ is representative of this.

The catalyst may be employed as pellets, disc, flakes, wafers, or any other convenient shape which will facilitate its use in the tubular reactors employed for this type of vapor phase reaction. For example the catalyst may be prepared as tablets having a hole or bore therethrough as disclosed in U.S. Pat. No. 4,283,307 which is incorporated herein. The material can be deposited on a carrier. Although fixed bed tubular reactors are standard for this type of reaction, fluidized beds are frequently used for oxidation reactions, in which case the catalyst particle size would be on the order of about 10 to 150 microns.

The use of this class of catalyst for the partial oxidation of $C_4$-$C_{10}$ hydrocarbons to the corresponding anhydrides is generally recognized. They have been widely considered for the conversion of normal $C_4$ hydrocarbons, both the alkane, n-butane, and alkene, n-butene, for the production of maleic anhydride, which has a wide commercial usage.

The oxidation of the n-$C_4$ hydrocarbon to maleic anhydride may be accomplished by contacting, e.g., n-butane in low concentrations in oxygen with the described catalyst. Air is entirely satisfactory as a source of oxygen, but synthetic mixtures of oxygen and diluent gases, such as nitrogen, also may be employed. Air enriched with oxygen may be employed.

The gaseous feed stream to the standard tubular oxidation reactors normally will contain air and about 0.5 to about 2.5 mole percent hydrocarbons such as n-butane. About 1.0 to about 2.0 mole percent of the n-$C_4$ hydrocarbon are satisfactory for optimum yield of product for the process of this invention. Although higher concentrations may be employed, explosive hazards may be encountered except in fluidized bed reactors where concentrations of up to about 4 or 5 mole % can be used without explosive hazard. Lower concentrations of $C_4$, less than about one percent, of course, will reduce the total productivity obtained at equivalent flow rates and thus are not normally economically employed.

The flow rate of the gaseous stream through the reactor may be varied within rather wide limits but a preferred range of operations is at the rate of about 50 to 300 grams of $C_4$ per liter of catalyst per hour and more preferably about 100 to about 250 grams of $C_4$ per liter of catalyst per hour. Residence times of the gas stream will normally be less than about 4 seconds, more preferably less than about one second, and down to a rate where less efficient operations are obtained. The flow rates and residence times are calculated at standard conditions of 760 mm. of mercury and at 25° C. A preferred feed for the catalyst of the present invention for conversion to maleic anhydride is a n-$C_4$ hydrocarbon comprising a predominant amount of n-butane and more preferably at least 90 mole percent n-butane.

A variety of reactors will be found to be useful and multiple tube heat exchanger type reactors are quite satisfactory. The tubes of such reactors may vary in diameter from about ¼ inch to about 3 inches, and the length may be varied from about 3 to about 10 or more feet. The oxidation reaction is an exothermic reaction and, therefore, relatively close control of the reaction temperature should be maintained. It is desirable to have the surface of the reactors at a relatively constant temperature and some medium to conduct heat from the reactors is necessary to aid temperature control. Such media may be Woods metal, molten sulfur, mercury, molten lead, and the like, but it has been found that eutectic salt baths are completely satisfactory. One such salt bath is a sodium nitrate-sodium nitrite-potassium nitrite eutectic constant temperature mixture. An additional method of temperature control is to use a metal block reactor whereby the metal surrounding the tube acts as a temperature regulating body. As will be recognized by one skilled in the art, the heat exchange medium may be kept at the proper temperature by heat exchangers and the like. The reactor or reaction tubes may be iron, stainless steel, carbon-steel, nickel, glass tubes such as Vycor and the like. Both carbon steel and nickel tubes have excellent long life under the conditions for the reactions described herein. Normally, the reactors contain a preheat zone of an inert material such as ¼ inch Alundum pellets, inert ceramic balls, nickel balls or chips and the like, present at about one-half to one-tenth the volume of the active catalyst present.

The temperature of reaction may be varied within some limits, but normally the reaction should be conducted at temperatures within a rather critical range. The oxidation reaction is exothermic and once reaction is underway, the main purpose of the salt bath or other media is to conduct heat away from the walls of the reactor and control the reaction. Better operations are normally obtained when the reaction temperature employed is no greater than about 100° C. above the salt bath temperature. The temperature in the reactor, of course, will also depend to some extent upon the size of the reactor and the $C_4$ concentration. Under usual operating conditions, in a preferred procedure, the temperature in the center of the reactor, measured by thermocouple, is about 365° C. to about 550° C. The range of temperature preferably employed in the reactor, measured as above, should be from about 380° C. to about 515° C. and the best results are ordinarily obtained at temperatures from about 390° C. to about 415° C. Described another way, in terms of salt bath reactors with carbon steel reactor tubes about 1.0 inch in diameter, the salt bath temperature will usually be controlled between about 350° C. to about 550° C. Under normal conditions, the temperature in the reactor ordinarily should not be allowed to go above about 470° C. for extended lengths of time because of decreased yields and possible deactivation of the catalyst.

Generally the improved catalyst of the present invention is more active and operates at a lower temperature and higher weight yield than prior anhydrous process PVO catalysts.

The reaction may be conducted at atmospheric, super-atmospheric or below atmospheric pressure. The exit pressure will be at least slightly higher than the ambient pressure to insure a positive flow from the reaction. The pressure of the inert gases must be sufficiently high to overcome the pressure drop through the reactor.

The maleic anhydride may be recovered in a number of ways well known to those skilled in the art. For example, the recovery may be by direct condensation or by adsorption in suitable media, with subsequent separation and purification of the maleic anhydride.

EXAMPLES

The method in which the catalyst is prepared is important. The following typical catalysts preparative procedures illustrate typical catalyst work up using the information discussed above. The crystallization carried on in the two reflux steps as described are easily controlled and reproduced to obtain the catalyst.

EXAMPLE 1 Comparative

Into a 12 liter round flask equipped with a mechanical stirrer, a gas inlet tube, thermowell, Dean stark trap with a condenser, and a heating mantle were charged 3920 ml anhydrous isobutanol and 627 grams $V_2O_5$. About 3.45 lb hydrogen chloride gas was bubbled into the stirred suspension. The reaction temperature was maintained at 40±3° C. To the resulting dark redbrown solution was added 9.3 grams anhydrous zinc chloride, 2.92 grams lithium chloride, 12.90 grams molybdenum trioxide and a solution of phosphoric acid prepared from 193.7 grams $P_2O_5$ dissolved in 590 grams of 87.5% phosphoric acid. An additional 852 ml of anhydrous isobutanol were added to the reaction mixture. Heat was supplied and about 105 ml liquid were removed before the reaction mixture was placed under reflux conditions for 1 hour. Thereafter, about 3800 ml of distillate was removed with the slurry temperature reaching 118° C., resulting in a thick black slurry, which was gummy and difficult to handle, causing loses in the product recovery step. The thick slurry was then dried for 16 hours at 150° C. under air. The dry cake was then crushed and calcined in air at 260° C. for 3 hours. Following this procedure the slurry temperature increased from 106 ° C. at the start of distillation to 118° C. when it was completed. The calcined product had a 24% crystallinity by X-ray diffraction analysis. The calcined powder was mixed with 3% graphite and formed into 3/16"×3/16" tablets with a hole struck therethrough.

EXAMPLE 2 Uniform Crystallization Conditions

The procedure of Example 1 were followed until after the first reflux for 1 hour. After the first hour of reflux about 1910 ml solvent were removed by distillation. The slurry temperature was 112° C. at this stage. The distillation was stopped and the reaction mixture was refluxed for 1 hour during which the slurry temperature dropped to 108 ° C. At the start of the second reflux step a very small amount of crystals were observed which acted as nucleation sites for the crystallization. At the end of the second reflux period most of the crystallization had been completed. The distillation was then resumed and was completed after about 1100 ml additional solvent was removed during which time the slurry temperature increased to 113° C. by the end of the distillation step. The thick slurry was dark green and not gummy and easy to handle and to recover. The catalyst was dried and calcined as in Example 1. The calcined product had 48% crystallinity by X-ray diffraction peak analysis.

EXAMPLE 3 Different Molybdenum Source

The procedure of Example 2 was followed except that the primary alcohol volume was 3564 ml, the secondary alcohol volume was 774 ml and the molybdenum trioxide promoter was replaced with 17.67 g of 12-molybdophosphoric acid. About 2460 ml solvent distilled off after the first reflux period. The temperature of the slurry dropped 3° C. during the second reflux period. The catalyst was dried and calcined as in Example 1. The calcined product had a 73% crystallinity by X-ray diffraction peak analysis.

EXAMPLE 4 Mixed Solvents

The procedure of Example 3 was used to prepare the catalyst except that 15% of the isobutanol was replaced with 2-butanol. In this procedure the temperature of the slurry dropped 6° C. from the beginning to the end of the second reflux period. About 3300 ml solvent were distilled off before transferring the slurry to the drying oven. The slurry was not gummy, but was easy to handle and to recover. The catalyst was dried and calcined as in Example The calcined product had a 78% crystallinity as measured by X-ray diffraction peak analysis.

EXAMPLE 5 Mixed solvents

The procedure of Example 2 was followed except that in addition to the secondary isobutanol volume of 774 ml, 434 ml of 4-methyl 2-pentanone was also added. The second reflux period started after distilling off 2350 ml and was increased to 2 hours. In this procedure, the temperature of the slurry dropped by 4° C. from the beginning to the end of the second reflux period. About 3775 ml solvent were distilled off before transferring the slurry to the drying oven. The catalyst was dried and calcined as in Example 1. The calcine product had a crystallinity of 43%

Each of the examples catalyst are tested for activity and selectivity in the n-butane partial oxidation to maleic anhydride. Air in the feed is balanced with the % butane used in the reaction.

The catalyst is conditioned for use by placing the catalyst (tablets) in the tubular reactor of a fixed bed reactor and carrying out the conditioning.

The reactor is 5 foot stainless steel tube, 1 inch outside diameter, packed with a 3.5 foot catalyst bed (3/16"×3/16" tablet with a 1/16" center hole) and with inert ¼ inch Alundum pellets on top of the catalyst material to a height 33% of the height of the catalyst. The reactors are encased in a 7% sodium nitrate; 40% sodium nitrite 53% potassium nitrite eutectic mixture constant temperature salt bath. The catalyst is loaded in the reactor and conditioned by a slow bring-up of the catalyst to operating temperature at the rate of 5° to 20° C. per hour achieved by heating the reactor and adjusting the gas flow from 0.5 to 1.5 mole % butane in air at an initial flow of GHSV of $900^{-1}$ hours up to $2500^{-1}$ hours while maintaining a desired conversion level, e.g., about 75 mole %, the procedure requiring in general several days. The initial temperature of the salt bath is about 250° C. (a point where the salt bath is molten).

The throughput is achieved in relation to the maximum salt bath temperature and maximum hot spot. The hot spot is determined by a probe through the center of the catalyst bed. The temperature of the salt bath can be adjusted to achieve the desired relationship between the conversion and flow rates of the n-C4/air mixture (e.g. gas hourly space velocity - GHSV). The flow rate is adjusted to conversion and the temperature relations given above.

The C, S and Y used in reporting reaction results have the following meaning and relationship C(conversion) x S(selectivity) =Y(yield); where:

$$\% \text{ Conversion} = \frac{\text{moles n-butane reacted}}{\text{moles n-butane fed}} \times 100$$

$$\% \text{ Selectivity} = \frac{\text{moles maleic anhydride produced}}{\text{moles n-butane reacted}} \times 100$$

The term "weight yield" means the amount of maleic anhydride produced from a given amount of n-butene, calculated as follows:

$$\text{wt yield} = \frac{98 \text{ (mole wt of maleic anhydride)}}{58 \text{ (mole wt of butane)}} \times \text{mole \% yield}$$

Percent crystallinity is determined by comparing the intensity of the 2.94 d reflection of the dried catalyst material to that of a secondary standard of $VOHPO_4 \cdot \frac{1}{2} H_2O$.

The results from the testing of each of the samples is shown in TABLE I below. The results in TABLE 1 demonstrate that the catalyst prepared in Example 2 to 5 produce higher MAN yield than the catalyst in comparative Example 1. Furthermore, the hot spot in Example 1 is much higher than for the catalysts in Examples 2-5 by more than 50° C. The temperature difference between the hot spot and the salt bath is 100° C. for the catalyst in comparative Example 1 and is only 31°-38° C. for the catalysts Examples 2-5. Lower hot spots and a smaller difference between the hot spot and the salt bath temperatures are more desirable for commercial operations. The catalyst in Example 5 activated very rapidly indicating that the presence of a cosolvent can improve the activation rate and the performance of the catalyst.

TABLE I[(1)]

| EXAM. | HRS ON STM | TEMP. °C. BATH | TEMP. °C. HOT SPOT | n-BUTANE mole | GHSV hr−1 | CONV. mol % | SELEC mol % | YIELD wt % |
|---|---|---|---|---|---|---|---|---|
| 1 | 1056 | 371 | 471 | 1.3 | 2500 | 80.1 | 66.4 | 89.8 |
| 2 | 1113 | 382 | 413 | 1.3 | 2500 | 79.3 | 70.7 | 94.5 |
| 3 | 1079 | 382 | 420 | 1.33 | 2500 | 80.5 | 67.2 | 91.3 |
| 4 | 1052 | 384 | 415 | 1.3 | 2500 | 80.3 | 69.7 | 94.4 |
| 5 | 869 | 388 | 414 | 1.29 | 2500 | 80.1 | 69.6 | 94.0 |

[(1)] 1" × 5' Reactor; 3.5' bed with thermowell; 3/16" × 3/16" tablets with 1/16" hole in center.

The invention claimed is:

1. In a method for preparing a phosphorus/vanadium/zinc/lithium/molybdenum mixed oxide oxidation catalyst comprising reducing vanadium in the +5 valence state in a substantially anhydrous organic solvent to a valence of less than +5 and digesting said reduced vanadium in a reaction mixture comprising concentrated phosphoric acid and the solvent, wherein the improvement comprises (1) refluxing the reaction mixture for a first period, (2) removing a portion of the solvent from the reaction mixture by distillation to initiate crystallization of the catalyst, (3) refluxing the reaction mixture again for a second period during which the crystallization of the catalyst is substantially completed and (4) removing the remainder of the solvent from the reaction mixture, wherein zinc, lithium, and molybdenum components are added to the reaction mixture prior to the initiation of crystallization.

2. The method according to claim 1 wherein between 20-85 percent of the solvent is removed by distillation to initiate nucleation prior to beginning said second period.

3. The method of according to claim 1 wherein the first period and the second period each comprises about 15 minutes to 10 hours.

4. The method according to claim 1 wherein about 40-85 percent of the solvent is removed by distillation after said second period.

5. A method for preparing a phosphorus/vanadium/zinc/lithium/molybdenum mixed oxide oxidation catalyst comprising the steps of:
admixing a +5 valence vanadium compound with an organic solvent, contacting said mixture with gaseous HCl until the valence of vanadium is reduced to less than +5 at a temperature in the range of 35° to 60° C., digesting said reduced vanadium, a zinc compound, a lithium compound and a molybdenum compound in concentrated phosphoric acid of about 98 to 101% H$_3$PO$_4$ by a first reflux step,
adding a molybdenum compound in the mole ratio of Mo/V of 0.005 to 0.025:1 during said digesting,
removing a first portion of said organic solvent from said digested mixture by distillation to initiate crystallization,
refluxing said solvent in a second reflux step until crystallization is substantially complete,
removing a second portion of said organic solvent from said digested mixture by distillation to form a slurry of mixed oxides and organic solvent,
recovering a dried mixed oxide composition and heating said dried mixed oxide composition at a temperature in the range of 200° to 400° C. for a sufficient period to improve the catalytic properties of the composition.

6. The method according to claim 5 wherein said valence is reduced at a temperature of about 40° C.

7. The method according to claim 5 wherein said first reflux step is maintained for about 1 hour.

8. The method according to claim 5 wherein said second reflux step is maintained for about 1 hour.

9. The method according to claim 5 wherein said first portion comprises about 20-85% of said solvent.

10. The method according to claim 5 wherein said second portion comprises about 40-85% of remaining solvent.

11. The method according to claim 5 wherein said solvent comprises isobutanol.

12. The method according to claim 5 wherein said solvent comprises a mixture of organic solvents.

13. The method according to claim 12 wherein said solvent comprises about 2-butanol and from 5 to 50% isobutanol.

14. The method according to claim 12 wherein said solvent comprises 5-50% 4-methyl-2-pentanol and isobutanol.

* * * * *